United States Patent
Kay et al.

(10) Patent No.: US 6,303,362 B1
(45) Date of Patent: Oct. 16, 2001

(54) ADENOVIRAL VECTOR AND METHODS FOR MAKING AND USING THE SAME

(75) Inventors: Mark A. Kay, Stanford, CA (US); Hiroyuki Mizuguchi, Tokyo (JP)

(73) Assignees: The Board of Trustees of the Leland Stanford Junior University, Palo Alto, CA (US); University of Washington, Seattle, WA (US)

(*) Notice: Subject to any disclaimer, the term of this patent is extended or adjusted under 35 U.S.C. 154(b) by 0 days.

(21) Appl. No.: 09/428,292

(22) Filed: Oct. 27, 1999

Related U.S. Application Data (60) Provisional application No. 60/109,057, filed on Nov. 19, 1998.

(51) Int. Cl.$^7$ .................................................... C12N 7/00
(52) U.S. Cl. ..................... 435/235.1; 424/93.2; 424/93.6; 435/5; 435/69.1; 435/91.4; 435/173.3; 435/252.3; 514/44; 536/23.72; 935/23
(58) Field of Search ................. 424/93.2, 93.21, 424/93.6; 435/5, 69.1, 69.7, 71.2, 91.4, 173.3, 235.1, 252.3, 325, 455; 514/44; 536/23.72; 935/22, 23

(56) References Cited

U.S. PATENT DOCUMENTS

| | | |
|---|---|---|
| 5,075,227 * | 12/1991 | Hagen ............................ 435/172.3 |
| 5,354,678 | 10/1994 | Lebkowski et al. . |
| 5,585,362 | 12/1996 | Wilson et al. . |
| 5,589,377 | 12/1996 | Lebkowski et al. . |
| 5,616,326 | 4/1997 | Spibey . |
| 5,670,488 | 9/1997 | Gregory et al. . |
| 5,700,470 | 12/1997 | Saito et al. . |
| 5,707,618 | 1/1998 | Amentano et al. ............. 424/93.21 |
| 5,731,172 | 3/1998 | Saito et al. . |
| 5,747,072 | 5/1998 | Davidson et al. . |
| 5,756,283 | 5/1998 | Wilson et al. . |
| 5,789,390 | 8/1998 | Descamps et al. . |
| 5,820,868 | 10/1998 | Mittal et al. . |
| 5,837,484 | 11/1998 | Trempe et al. . |
| 5,843,742 | 12/1998 | Natsoulis et al. . |
| 5,851,806 | 12/1998 | Kovesdi et al. . |
| 5,858,351 | 1/1999 | Podsakoff et al. . |
| 5,869,037 | 2/1999 | Crystal et al. . |
| 5,871,982 | 2/1999 | Wilson et al. . |
| 5,877,011 | 3/1999 | Amentano et al. . |
| 5,880,102 | 3/1999 | George et al. . |
| 5,885,808 | 3/1999 | Spooner et al. . |
| 5,891,690 | 4/1999 | Massie . |
| 5,919,676 | 7/1999 | Graham et al. . |
| 5,922,576 | 7/1999 | He et al. . |
| 5,928,944 | 7/1999 | Seth et al. . |
| 5,932,210 | 8/1999 | Gregory et al. . |
| 5,952,221 | 9/1999 | Kurtzman et al. . |
| 5,962,311 | 10/1999 | Wickham et al. . |
| 5,962,313 | 10/1999 | Podsakoff et al. . |

OTHER PUBLICATIONS

Berkner et al. (1983) "Generation of Adenovirus by Transfection of Plasmids," *Nuc. Acids Res.*, vol. 11(17):6003–6021.

Bett et al. (1994) "An Efficient and Flexible System for Construction of Adenovirus Vectors with Insertions or Deletions in Early Regions 1 and 3," *Proc. Natl. Acad. Sci. USA*, vol. 91:8802–8806.

Chartier et al. (1996) "Efficient Generation of Recombinant Adenovirus Vectors by Homologous Recombination in *Escherichia coli*," *Journal of Virology*, vol. 70(7):4805–4810.

Crouzet et al. (1997) "Recombinational Construction in *Escherichia coli* of Infectious Adenoviral Genomes," *Proc. Natl. Acad. Sci. USA*, vol. 94:1414–1419.

Gilardi et al. (1990) "Expression of Human $\alpha_1$–antitrypsin Using a Recombinant Adenovirus Vector," *FEBS Letters*, vol. 267(1):60–62.

He et al. (1998) "A Simplified System for Generating Recombinant Adenoviruses," *Proc. Natl. Acad. Sci. USA* vol. 95:2509–2514.

Ketner et al. (1994) "Efficient Manipulation of the Human Adenovirus Genome as an Infectious Yeast Artificial Chromosome Clone," *Proc. Natl. Acad. Sci. USA*, vol. 91:6186–6190.

Miyake et al. (1996) "Efficient Generation of Recombinant Adenoviruses Using Adenovirus DNA–Terminal Protein Complex and a Cosmid Bearing the Full–Length Virus Genome," *Proc. Natl. Acad. Sci. USA*, vol. 93:1320–1324.

Rosenfeld et al. (1991) "Adenovirus–Mediated Transfer of a Recombinant $\alpha$1–Antitrypsin Gene to the Lung Epithelium in Vivo," *Science*, vol. 252:431–434.

(List continued on next page.)

*Primary Examiner*—Jeffrey Stucker
*Assistant Examiner*—Ulrike Winkler
(74) *Attorney, Agent, or Firm*—Bret E. Field; Bozicevic, Field & Francis (57) ABSTRACT

In vitro methods for making a recombinant adenoviral genome, as well as kits for practicing the same and the recombinant adenovirus vectors produced thereby, are provided. In the subject methods, the subject genomes are prepared from first and second vectors. The first vector includes an adenoviral genome having an E region deletion and three different, non-adenoviral restriction endonuclease sites located in the E region. The second vector is a shuttle vector and includes an insertion nucleic acid flanked by two of the three different non-adenoviral restriction endonucleases sites present in the first vector. Cleavage products are prepared from the first and second vectors using the appropriate restriction endonucleases. The resultant cleavage products are then ligated to produce the subject recombinant adenovirus genome. The subject adenoviral genomes find use in a variety of application, including as vectors for use in a variety of applications, including gene therapy.

15 Claims, 2 Drawing Sheets

OTHER PUBLICATIONS

Conley et al. Recombination–dependent recircularization of linearized pBR322 plasmid DNA following transformation of *E. coli*. Molecular General Genetics. vol. 194 (1984) pp. 211–218.*

Sambrook et al. Molecular cloning, a laboratory manual. Cold Spring Harbor Laboratory Press, 1989.*

Majumder et al. Recombinant enrichment by exploitation of restriction sites with interrupted palindromes: design, synthesis and incorporation of zero–background linkers in cloning and expression vectors. GENE vol. 151 (1994) pp. 147–151.*

Majumder et al. Background–minimized cassette mutagenesis by PCR using cassette–specific selection markers. PCR Methods and Applications vol. 4, No. 4 (1995) pp. 212–218.*

Fisher et al., Virology (1996) 217:11–22.

Gorziglia et al., J. Virology (Jun. 1996) 70:4173–4178.

Trapnell et al., Curr. Opin. Biol. (1994) 5:617–625.

* cited by examiner

ADENOVIRAL VECTOR AND METHODS FOR MAKING AND USING THE SAME

CROSS REFERENCE TO RELATED APPLICATIONS

Pursuant to 35 U.S.C. § 119 (e), this application claims priority to the filing date of the United States Provisional Patent Application Ser. No. 60/109,057 filed Nov. 19, 1998, the disclosure of which is herein incorporated by reference.

ACKNOWLEDGMENT

This invention was made with United States Government support under Grant No. NIH DX 49022 awarded by National Institutes of Health. The United States Government has certain rights in this invention.

INTRODUCTION

1. Field of the Invention

The field of this invention is nucleic acid vectors, particularly adenoviral based vectors.

2. Background of the Invention

The introduction of an exogenous nucleic acid sequence (e.g. DNA) into a cell, a process known as "transformation," plays a major role in a variety of biotechnology and related applications, including research, synthetic and therapeutic applications. Research applications in which transformation plays a critical role include the production of transgenic cells and animals. Synthetic applications in which transformation plays a critical role include the production of peptides and proteins. Therapeutic applications in which transformation plays a key role include gene therapy applications. Because of the prevalent role transformation plays in the above and other applications, a variety of different transformation protocols have been developed.

In many transformation applications, it is desirable to introduce the exogenous DNA in a manner such that it is incorporated into a target cell's genome. One means of providing for genome integration is to employ a vector that is capable of homologous recombination. Techniques that rely on homologous recombination can be disadvantageous in that the necessary homologies may not always exist; the recombination events may be slow, etc. As such, homologous recombination based protocols are not entirely satisfactory.

Accordingly, alternative viral based transformation protocols have been developed, in which a viral vector is employed to introduce exogenous DNA into a cell and then subsequently integrate the introduced DNA into the target cell's genome. Viral based vectors finding use include retroviral vectors, e.g. Maloney murine leukemia viral based vectors. Other viral based vectors that find use include, HSV derived vectors, sindbis derived vectors, etc. One type of viral vector of particular interest is the adenovirus derived vector.

Recombinant adenovirus vectors have been shown to have great promise for the gene transfer in basic research as well as clinical treatment of many diseases.They can transduce foreign genes efficiently into both cultured cells and many target organs in vivo. There are more forty different serotypes of adenovirus (Ad) identified. The Ad type 5 genome has been most commonly used to make recombinant Ad vector. The genome of human Ad is a linear 36 kb, double-stranded DNA genome that encodes more than 50 gene products. In the first generation Ad vector, the early region 1 (E1) is replaced by the foreign gene and the virus propagated in an E1-transcomplementing cell line such as 293. By deleting E1 and early region 3 (E3) sequences up to about 8 kb of foreign gene can be inserted. However, in vitro manipulation of Ad DNA is difficult. Unique and useful restriction sites are limited because of the large size of the genome, making the construction of Ad vector relatively labor intensive. Two standard methods to make E1-deleted Ad vector have been developed: an in vitro ligation method and a homologous recombination method in 293 cells.

The in vitro ligation method uses whole viral DNA genomes and the plasmid containing the left end of Ad with the right inverted terminal repeat (ITR), the packaging signal and E1A enhancer sequence (map unit; 0 to 1.3). After the gene of interest is inserted into the downstream of the viral sequence of the plasmid, the fragment containing viral sequence and gene of interest is excised and ligated to the unique ClaI site (map unit; 2.6), replacing a portion of the viral E1 region. Then, the ligated DNA is directly transfected into 293 cells to make recombinant virus. However, this method is rarely used today because the efficiency is low and the recombinant virus requires purification of contaminating wild type and transgene null viruses related to incomplete restriction digestion and self-religation.

One system using homologous recombination uses two plasmids with overlapping fragments that recombine in vivo. The first plasmid contains the entire Ad genome with a deletion of the DNA packaging and E1 region. The second plasmid contains right ITR, packaging signal and overlapping sequence with the first plasmid. After the gene of interest is introduced into the second plasmid, the two plasmids are co-transfected into 293 cells. The virus, which is produced by the recombination in 293 cells, is isolated through plaque purification. The major limitation to this approach is that the recombination event occurs at a low frequency.

Newer methods for adenoviral preparation are based on homologous recombination of two plasmids using yeast artificial chromosomes or bacteria. These methods, while more efficient, are more complex. The YAC system requires yeast culture and manipulation while the *E.coli* system requires three step transformations using an additional non-convential host bacterial strain (BJ5183recBCsbcBC).

Accordingly, there is continued interest in the development of new methods for preparing recombinant adenoviral vectors. Of particular interest would be the development of a method which is highly efficient and yet requires a minimum number of steps.

Relevant Literature

U.S. Patents of interest include: U.S. Pat. Nos. 5,962,313; 5,962,311; 5,952,221; 5,932,210; 5,928,944; 5,922,576; 5,919,676; 5,891,690; 5,885,808; 5,880,102; 5,877,011; 5,871,982; 5,869,037; 5,858,351; 5,851,806; 5,843,742; 5,837,484; 5,820,868; 5,789,390; 5,756,283; 5,747,072; 5,731,172; 5,700,470; 5,670,488; 5,616,326; 5,589,377; 5,585,362; and 5,354,678.

Other references of interest include: Berkner, et al., (1983). Generation of adenovirus by transfection of plasmids. Nucleic Acids Res. 11, 6003–6020; Bett, et al. (1994). An efficient and flexible system for construction of adenovirus vectors with insertions or deletions in early regions 1 and 3. Proc Natl Acad Sci U S A. 91, 8802–6; Chartier, et al. (1996). Efficient generation of recombinant adenovirus vectors by homologous recombination in Escherichia coli. J Virol. 70, 4805–4810; Crouzet, et al. (1997). Recombinational construction in Escherichia coli of infectious adenoviral genomes. Proc Natl Acad Sci U S A. 94, 1414–1419; Gilardi et al. (1990). Expression of human alpha 1-antitrypsin using a recombinant adenovirus vector. FEBS Lett. 267, 60–2; He, et al. (1998). A simplified system for generating recombinant adenoviruses. Proc Natl Acad Sci U S A. 95, 2509–2514; Ketner, et al. (1994). Efficient manipulation of the human adenovirus genome as an infectious yeast artificial chromosome clone. Proc Natl Acad Sci U S A. 91, 6186–6190; Miyake, et al. (1996). Efficient generation of recombinant adenoviruses using adenovirus DNA-terminal protein complex and a cosmid bearing the full-length virus genome. Proc Natl Acad Sci U S A. 93, 1320–1324; and Rosenfeld, et al. (1991). Adenovirus-mediated transfer of a recombinant alpha 1-antitrypsin gene to the lung epithelium in vivo. Science. 252, 431–4.

SUMMARY OF THE INVENTION

In vitro methods for making a recombinant adenovirus genome, as well as kits for practicing the same and the recombinant adenovirus vectors produced thereby, are provided. In the subject methods, the subject genomes are prepared from first and second vectors. The first vector includes an adenoviral genome having an E region deletion and three different, non-adenoviral restriction endonuclease sites located in the E region. The second vector is a shuttle vector and includes a non adenoviral nucleic acid (which is desired to be inserted into the adenoviral genome, i.e. an insertion nucleic acid) flanked by two of the three different non-adenoviral restriction endonuclease sites present in the first vector. Cleavage products are prepared from the first and second vectors using the appropriate restriction endonucleases. The resultant cleavage products are then ligated to produce the subject recombinant adenovirus genome. The subject adenoviral genomes find use in a variety of applications, including as vectors for use in a variety of applications, e.g. gene therapy.

BRIEF DESCRIPTION OF THE DRAWINGS

FIG. 1 Construction of recombinant adenovirus vectors by a simple in vitro ligation method.

DESCRIPTION OF THE SPECIFIC EMBODIMENTS

In vitro methods for making a recombinant adenovirus genome, as well as kits for practicing the same and the recombinant adenovirus vectors produced thereby, are provided. In the subject methods, the subject genomes are prepared from first and second vectors. The first vector includes an adenoviral genome having an E region deletion and three different, non-adenoviral restriction endonuclease sites located in the E region. The second vector is a shuttle vector and includes an insertion nucleic acid flanked by two of the three different non-adenoviral restriction endonuclease sites present in the first vector. Cleavage products are prepared from the first and second vectors using the appropriate restriction endonucleases. The resultant cleavage products are then ligated to produce the subject recombinant adenovirus genome. The subject adenoviral genomes find use in a variety of applications, including th e production of recombinant adenoviral vectors for use in a variety of applications, e.g. gene therapy.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a,""an," and "the" include plural reference unless the context clearly dictates otherwise. Unless defined otherwise, all technical and scientific terms used herein have the same meaning as commonly understood to one of ordinary skill in the art to which this invention belongs.

METHODS OF PREPARING THE SUBJECT VECTORS

As summarized above, novel methods of preparing adenoviral nucleic acid vectors are provided by the subject invention. In the subject methods, first and second cleavage products are produced from initial first and second vectors, where the first cleavage product includes the adenoviral genome sequences of interest and the second cleavage produce includes the desired non-adenoviral nucleic acid insert, i.e. a non-adenoviral nucleic acid which is desired to be inserted into the adenoviral genome. The cleavage products are then combined under conditions such that the adenoviral vector is produced. Critical features of the subject methods include the nature of the first and second vectors and the nature of the restriction endonuclease employed in the subject methods. The subject methods, including these critical features, are now described in greater detail.

As indicated above, the first vector comprises an adenoviral genome. By adenoviral genome is meant the genome of an adenovirus, where adenoviral type 5 genomes are of particular interest. While in principle any type of vector may be employed, the first vector is typically a plasmid. A critical feature of the first vector employed in the subject methods is that the adenoviral genome of the first vector includes an E gene deletion. By E gene deletion is meant a deletion or absence of a portion of the adenoviral genome where the adenoviral E genes are present, e.g. E1, E2, E3, E4. The size of the E gene deletion of the subject first vector may vary, but in many embodiments typically ranges from about 1.0 to 35.0 kb, usually from about 1.0 to 12 kb and often from about 3 to 8 kb. In many embodiments, the E gene deletion includes a deletion of one of the E1, E3 and/or E4 genes, where in certain embodiments the deletion is characterized by a deletion of the E1 and E3 genes or a portion thereof, i.e. and E 1/E3 deletion; and in other embodiments the deletion is a deletion of the E1 and E4 genes or a portion thereof, i.e. an E1/E4 deletion.

The first vector is further characterized by the presence of first, second and third endonuclease restriction sites, where these sites are present in the E gene deletion region of the vector. The first, second and third restriction endonuclease sites are sites that are not found in the wild type adenoviral genome corresponding to the adenoviral genome present in the vector. For example, in those embodiments where the adenoviral genome is a type 5 adenoviral genome, the first, second and third restriction endonuclease sites present in the E deletion region of the adenoviral genome are ones that are not found in the wild type type 5 adenoviral genome. Furthermore, the first, second and third restriction endonuclease sites appear only once on the first vector. As such, they are unique on the first vector. In addition, the first, second and third restriction endonuclease sites are different from each, i.e. they are recognized and cleaved by different restriction endonucleases. The order of the restriction endonuclease sites going in the direction from the E region to the remainder of the adenoviral genome is: first, second and third.

Any convenient restriction sites may be used as the first, second and third sites, so long as the restriction sites meet the above criteria. Generally, the restriction sites range in length from about 4 to 30, usually from about 4 to 11 and more usually from about 4 to 6 bp in length. Restriction sites of interest include those recognized by the following restriction endonucleases: I-ceuI, SwaI, PI-SceI, I-SceI, I-PpoI, ClaI, AsuII (Csp45I) and the like. In many embodiments of interest the restriction sites are the I-CeuI, PI-SceI and SwaI sites. In certain embodiments, the first and third restriction sites are selected from I-CeuI and PI-SceI, e.g. the first site is I-CeuI and the third site is PI-SceI or vice versa, and the second restriction site is SwaI.

The first vector also generally includes a selectable marker gene, where any suitable marker gene may be employed. In general, genes which confer resistance to antibacterial agents are of interest, where such genes include: $tet^r$, $amp^r$, $Cm^r$, $cat^r$, $kan^r$ $neo^r$ and the like.

In addition to the above components or features, the first vector further includes restriction sites flanking either end of the adenoviral genome, which restriction sites are employed to excise the recombinant adenoviral genome from its vector, as described in greater detail infra. These restriction sites may be the same or different. Any convenient restriction site may be employed, so long as it is not found in the adenoviral genome present on the vector, where suitable sites include I-ceuI, SwaI, PI-SceI, I-SceI, I-PpoI, ClaI, AsuII (Csp45I) and the like.

The first vector employed in the subject methods and described above may be fabricated using any convenient protocol. A suitable protocol for preparing various vectors which may serve as first vectors in the subject methods is provided in the experimental section, infra.

The second vector employed in the subject methods is a shuttle vector. While the shuttle vector may, in principle, be any kind of vector, the shuttle vector is typically a plasmid. The shuttle vector serves as the source of the non-adenoviral nucleic acid or insertion nucleic acid (i.e. the nucleic acid that is desired to be inserted into the adenoviral genome to produce the recombinant adenoviral gemone and viral vectors of the subject invention). In other words, the non-adenoviral nucleic acid or insertion nucleic acid includes the nucleic acid which is desired to be inserted into the adenoviral genome of the first vector. Typically, the insertion sequence includes a multiple cloning site, i.e. a region having a plurality of different restriction endonuclease sites, where the number of different restriction endonuclease sites may vary greatly, but is often between about 1 to 20, usually between about 3 to 10. The insertion nucleic acid may or may not include a nucleic acid that encodes a product which is expressed under appropriate conditions. In other words, the insertion nucleic acid or non-adenoviral nucleic acid may or may not include a transgene. When present, this product encoding nucleic acid or gene is located in one of the restriction sites of the multiple cloning site of the insertion nucleic acid. The length of the insertion nucleic acid may vary, but in many typically ranges from about 1.0 to 35.0 kb, usually from about 1.0 to 12 kb and often from about 3 to 8 kb.

Depending on the ultimate use of the adenoviral vector, a variety of different features may be present in the insertion nucleic acid of the shuttle vector, in addition to those described above. In many embodiments, the insertion nucleic acid is characterized by the presence of at least one transcriptionally active gene. By transcriptionally active gene is meant a coding sequence that is capable of being expressed under intracellular conditions, e.g. a coding sequence in combination with any requisite expression regulatory elements that are required for expression in the intracellular environment of the target cell whose genome is modified by integration of the transposon. As such, the transcriptionally active genes of the subject vectors typically include a stretch of nucleotides or domain, i.e. expression module, that includes a coding sequence of nucleotides in operational combination, i.e. operably linked, with requisite trascriptional mediation or regulatory element(s). Requisite transcriptional mediation elements that may be present in the expression module include promoters, enhancers, termination and polyadenylation signal elements, splicing signal elements, and the like.

Preferably, the expression module includes transcription regulatory elements that provide for expression of the gene in a broad host range. A variety of such combinations are known, where specific transcription regulatory elements include: SV40 elements, as described in Dijkema et al., EMBO J. (1985) 4:761; transcription regulatory elements derived from the LTR of the Rous sarcoma virus, as described in Gorman et al., Proc. Nat'l Acad. Sci USA (1982) 79:6777; transcription regulatory elements derived from the LTR of human cytomegalovirus (CMV), as described in Boshart et al., Cell (1985) 41:521; hsp70 promoters, (Levy-Holtzman ,R. and I. Schechter (Biochim. Biophys. Acta (1995) 1263: 96–98) Presnail, J. K. and M. A. Hoy, (Exp. Appl. Acarol. (1994) 18: 301–308) and the like.

In certain embodiments, the at least one transcriptionally active gene or expression module present in the insertion nucleic acid acts as a selectable marker. A variety of different genes have been employed as selectable markers, and the particular gene employed in the subject vectors as a selectable marker is chosen primarily as a matter of convenience. Known selectable marker genes include: the thimydine kinase gene, the dihydrofolate reductase gene, the xanthine-guanine phosporibosyl transferase gene, CAD, the adenosine deaminase gene, the asparagine synthetase gene, the antibiotic resistance genes, e.g. $tet^r$, $amp^r$, $Cm^r$ or $cat^r$, $kan^r$ or $neo^r$ (aminoglycoside phosphotransferase genes), the hygromycin B phosphotransferase gene, genes whose expression provides for the presence of a detectable product, either directly or indirectly, e.g. β-galactosidase, GFP, and the like.

In many embodiments, the at least one transcriptionally active gene or module encodes a protein that has therapeutic activity for the multicellular organism, where such include genes encoding the following products: factor VIII, factor IX, β-globin, low-density protein receptor, adenosine deaminase, purine nucleoside phosphorylase, sphingomyelinase, glucocerebrosidase, cystic fibrosis transmembrane regulator, α-antitrypsin, CD-18, omithine transcarbamylase, arginosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, interleukins, cytokines, small peptides etc, and the like Flanking the insertion sequence of the second or shuttle vector are the first and third restriction sites of the first vector. In other words, at one end of the insertion sequence of the second vector is either the first or third restriction site which is also present in the first vector. At the other end of the insertion sequence is the other of the first and third restriction sites. For example, where the first restriction site of the first vector is I-CeuI and the third restriction site of the first vector is PI-SceI, at one end of the insertion nucleic acid of the second vector is the I-CeuI site and at the other end of the insertion nucleic acid of the second vector is PI-SceI site.

For purposes of amplification and selection, the second vector may include one or more selectable marker genes, where genes of interest include genes that confer resistance to antibacterial agents. Representative marker genes include tet$^r$, amp$^r$, Cm$^r$, cat$^r$, kan$^r$, neo$^r$ and the like. In certain embodiments, the selectable marker gene of the second vector is different from the marker gene present on the first vector, e.g. where one desires to avoid an isolation step, as described in greater detail infra.

As with the first vector, the second vector, e.g. shuttle plasmid, employed in the subject methods and described above may be fabricated using any convenient protocol. A suitable protocol for preparing various shuttle vectors which may serve as second vectors in the subject methods is provided in the experimental section, infra.

The next step in the subject methods is to prepare cleavage products from the first and second vectors. Specifically, the next step requires the production of a first cleavage product from the first vector and a second cleavage product from the second vector. The first cleavage product that is produced from the first vector is a linear, double stranded nucleic acid that includes the adenoviral genome, as described above. The second cleavage product that is produced is a linear, double stranded nucleic acid that includes the insertion sequence of the second vector. The first and second cleavage products are produced by contacting the first and second vectors with the restriction endonucleases that cleave the first and third restriction endonuclease sites present on these first and second vectors, as described above. Thus, each of the first and second vectors is contacted with a pair of restriction nucleases, the first of which recognizes and cuts the first restriction site present on the vector and the second of which recognizes and cuts the third restriction endonuclease site present on the vector. For example, where the first restriction endonuclease site of each vector is I-CeuI and the third restriction endonuclease site of each vector is PI-SceI, both the first and third vectors are contacted with I-CeuI and PI-SceI under conditions such that each vector is cleaved at the first and third site to yield the first and second cleavage products, as described supra.

Contact of the first and second vectors with the first and third restriction endonucleases, as described above, results in the production of first and second cleavage product compositions, where these compositions include the first and second cleavage products, respectively. In certain embodiments, e.g. where the selectable marker gene of the first and second vectors are the same, it may be desirable to isolate at least one of the first and second, usually the second, cleavage products from their corresponding cleavage product compositions. Isolation of the cleavage product of interest can be accomplished using any convenient nucleic acid separation protocol, e.g. centrifugation, gel electrophoresis, or a combination thereof. By isolate is meant to prepare a composition that is enriched for the cleavage product. As such, in isolate compositions the amount of nucleic acid that is present in the composition and is not the cleavage product of interest, e.g. the second cleavage product, generally does not exceed about 60% and usually does not exceed about 50%.

Following cleavage product production, as well as cleavage product isolation, where desired, the first and second cleavage products are combined in vitro under ligation conditions sufficient to produce a ligation product that includes the first and second cleavage products described supra. In other words, the first and second cleavage products are combined under ligation conditions sufficient to produce a ligation product which includes both the adenoviral genome and the insertion sequence, where the insertion sequence originally of the second vector has been ligated into the E deletion region of the first vector by means of the complementary ends of the first and second cleavage products. Any convenient ligation conditions may be employed for this step, where ligation conditions are well known to those of skill in the art and representative conditions are disclosed in the experimental section infra.

The above step of combining the first and second cleavage products under ligation conditions results in the production of a ligation product composition that includes the above described ligation product. In many embodiments, the next step of the subject methods is to contact the ligation product composition with an enzyme that cleaves the second endonuclease restriction site of the original first vector, as described above, i.e. a second restriction endonuclease. For example, where the second restriction endonuclease site of the first vector was SwaI, the next step of the subject methods in these particular embodiments is to contact the ligation production composition with SwaI, e.g. by introducing a sufficient amount of SwaI into the ligation product composition. This contacting step is accomplished under conditions such that any nucleic acids comprising the second restriction site, e.g. null vectors, present in the ligation product composition, are cleaved. See e.g. the experimental section infra for a representative protocol for this step. By sufficient amount is meant the amount necessary to cleave substantially all, if not all, nucleic acids present in the composition that include the restriction site.

RECOMBINANT ADENOVIRAL VECTORS

The above steps result in the production of a recombinant adenoviral vector that has an adenoviral genome with an E region deletion, e.g. a type 5 adenoviral genome with an E1/E3 deletion, with an insertion nucleic acid, e.g. a nucleic acid encoding a product, in the E deletion region of the adenoviral genome. As mentioned above, while the vector may be any suitable type of vector in principle, this vector is generally a plasmid. Because of the manner in which this vector is produced, the vector is further characterized by having the first and third restriction sites flanking the insertion nucleic acid in the E gene deletion region of the vector. For example, in those embodiments where the first restriction site is I-CeuI and the third restriction site is PI-SceI, the adenoviral vector includes an adenoviral genome having an insertion nucleic acid present in the E region of the vector and flanked by I-CeuI and PI-SceI restriction sites. The E deletion region is characterized by the absence of at least part of at least one E gene, e.g. E1, E2, E3, E4, etc., where the length of the E deletion in many embodiments typically ranges from about 1.0 to 35.0 kb, usually from about 1.0 to 12 kb and often from about 3 to 8 kb. The size of the insertion nucleic acid present in the E deletion region in these embodiments typically ranges from about 1.0 to 35.0 kb, usually from about 1.0 to 12 kb and often from about 3 to 8 kb. The insertion nucleic acid may or may not encode a product. A number of different types of proteins may be encoded by the insertion sequence, where representative proteins are listed infra, and are also recited in the patents which are incorporated herein by reference in various locations of the specification. The recombinant adenoviral vectors are further characterized in that the adenoviral genome comprising the insertion nucleic acid is flanked by restriction endonuclease sites, as described above, where the endonuclease sites may be the same or different, e.g. PacI, ClaI, etc.

The recombinant adenoviral vectors produced according to the above described methods find use in, among other applications, the production of recombinant adenovirus particles or virions, which is turn find use in the transfer of nucleic acid into the genome of a cell, e.g. as is practiced in gene therapy applications, mutation analysis applications, and the like.

RECOMBINANT ADENOVIRUS AND METHODS FOR ITS PRODUCTION

Also provided by the subject invention are recombinant adenoviruses and methods for their production. The recombinant adenoviruses of the subject invention are characterized by having an adenoviral genome in which at least a portion of the E region has been deleted and replaced with an insertion nucleic acid. The adenoviral genome of the subject viruses is further characterized by the presence of the first and third restrictions sites, e.g. I-CeuI and PI-SceI, as described above.

The subject viruses may be produced using the recombinant adenoviral vectors, described supra. To produce the subject viruses using the subject recombinant adenoviral vectors, a suitable host cell is transfected with a linearized double stranded DNA derived from the vector and comprising the recombinant adenoviral genome. Generally, the linearized double stranded DNA that is employed in this step is produced by contacting the recombinant adenoviral vector with the restriction endonuclease(s) that cleave the sites flanking the genome in the vector. For example, where the adenoviral genome in the vector is flanked by PacI sites, the vector is contacted with PacI under conditions sufficient to cleave the vector and produce a linearized cleavage product that includes the recombinant adenoviral genome with the insertion sequence. Suitable host cells that are employed in the production of adenoviruses of the present invention are those that are transcomplementing for the E gene or genes which are missing/inactive in the recombinant adenoviral genome. The particular host cell employed varies depending on the nature of the E gene deletion region of the recombinant genome, but representative host cells that may be employed include: 293 cells, and the like. See also U.S. Pat. Nos. 5,928,944; 5,891,690; 5,872,005; 5,851,806; and 5,837,484; the disclosures of which are herein incorporated by reference. Transfection is carried out using any convenient protocol, where suitable protocols are known to those of skill in the art and a representative protocol is provided in the experimental section infra.

Following transfection, the transfected host cells are grown and recombinant adenovirus according to the subject invention is harvested therefrom, where any convenient protocol including standard protocols known to those of skill in the art may be employed for these steps. See e.g. the experimental section, infra.

METHODS OF USING THE SUBJECT RECOMBINANT ADENOVIRUSES

The subject recombinant adenoviruses can be used as vectors to stably insert a wide variety of endogenous and/or exogenous nucleic acids into the genome of a target cell (exogenous means a nucleic acid having a sequence that is not present in the target cell while endogenous means a nucleic acid that pre-exists in the target cell, prior to insertion). In many embodiments, the sequence of nucleotides present in the exogenous nucleic acid will be one that is not found in the genome of the target cell. The subject methods can be used with a variety of target cells. Target cells with which the subject vectors may be employed are generally animal or plant cells, where in many embodiments the target cells are animal cells. Of particular interest in many embodiments is the use of the subject vectors to target vertebrate cells, particularly avian cells, e.g. chicken cells; mammalian cells, including murine, porcine, ovine, equine, rat, dog, cat, monkey, and human cells; and the like.

In the methods of the subject invention, the adenovirus vector is contacted with a target cell under conditions sufficient for the adenovirus to insert its recombinant genome into the target cell. Any convenient protocol may be employed, where the protocol may provide for in vitro or in vivo introduction of the genome into the target cell. For example, where the target cell is a cell of an organism which has been removed from the organism, the recombinant virus may be contacted with the cell under cell culture conditions permissive of viability of the target cell. Alternatively, where the target cell or cells are part of a multicellular organism, the adenoviral vector may be administered to the organism or host in a manner such that the virus enters the organism and inserts its genome into the target cell(s). For example, virus may be injected into the organism or host, contacted with a mucosal surface of the host and the like.

The subject methods of stable integration of exogenous nucleic acid into the genome of a target cell using the subject adenoviral vectors find use in a variety of applications in which the stable integration of an exogenous nucleic acid into a target cell genome is desired. Applications in which the subject vectors and methods find use include: research applications, polypeptide synthesis applications and therapeutic applications. Each of these representative categories of applications is described separately below in greater detail.

Research Applications

Examples of research applications in which the subject vectors find use include applications designed to characterize a particular gene. In such applications, the vector is employed to insert a gene of interest into a target cell and the resultant effect of the inserted gene on the cell's phenotype is observed. In this manner, information about the gene's activity and the nature of the product encoded thereby can be deduced. The vectors can also be employed to identify and define DNA sequences that control gene expression, e.g. in a temporal (e.g. certain developmental stage) or spatial (e.g. particular cell or tissue type) manner. In such assays, the subject vectors are employed to stably integrate into the genome of a target cell a selectable marker gene, e.g. antibiotic resistance, LacZ, etc., where the vector lacks a sufficient promoter for the marker gene such that the marker is not significantly expressed, if at all, unless it is underneath an endogenous promoter element. If the marker gene is inserted into the target cell genome in sufficient relationship to an endogenous promoter sequence, it will be expressed.

From the resultant expression profile of the marker gene, the endogenous promoter that is mediating its expression can then be characterized. Yet another research application in which the subject vectors find use is in the identification and characterization of the results of gene expression studies. For example, a plurality of distinct vector targeted cells (or animals produced therefrom) are prepared in which the gene of interest is inserted into distinct locations in the genome of various targeted cells, where expression of the gene of interest is dependent on endogenous promoter mediation, i.e. where the gene of interest lacks a promoter or is coupled to only a weak promoter. By plurality is meant at least two, where the number usually ranges from about 2 to 5000, usually from about 2 to 200. This plurality of vector targeted cells may be produced by introducing the vector in a plurality of cells or taking a collection of pretargeted cells that are homogenous with respect to the insertion site of the gene, i.e. progeny of a single targeted cell, and then introducing transposase into one or more of, but not all of, the constituent members of the collection. The subject vectors can also be used to study integration mutants, where a gene of interest is inserted randomly into the genome and the affects of this random insertion of the targeted cell phenotype are observed. One can also employ the subject vectors to produce models in which overexpression and/or misexpression of a gene of interest is produced in a cell and the effects of this mutant expression pattern are observed. One can also use the subject vectors to readily clone genes introduced into a host cell via insertional mutagenesis that yields phenotypes and/or expression patterns of interest. In such applications, the subject vectors are employed to generate insertional mutants through random integration of DNA. The phenotype and/or expression pattern of the resultant mutant is then assayed using any convenient protocol.

Polypeptide Synthesis Applications

In addition to the above research applications, the subject vectors also find use in the synthesis of polypeptides, e.g. proteins of interest. In such applications, a vector that includes a gene encoding the polypeptide of interest in combination with requisite and/or desired expression regulatory sequences, e.g. promoters, etc., (i.e. an expression module) is introduced into the target cell that is to serve as an expression host for expression of the polypeptide. Following introduction and subsequent stable integration into the target cell genome, the targeted host cell is then maintained under conditions sufficient for expression of the integrated gene. Once the transformed host expressing the protein is prepared, the protein is then purified to produce the desired protein comprising composition. Any convenient protein purification procedures may be employed, where suitable protein purification methodologies are described in Guide to Protein Purification, (Deuthser ed.) (Academic Press, 1990). For example, a lysate may be prepared from the expression host expressing the protein, and purified using HPLC, exclusion chromatography, gel electrophoresis, affinity chromatography, and the like.

Therapeutic Applications

The subject vectors also find use in therapeutic applications, in which the vectors are employed to stably integrate a therapeutic nucleic acid, e.g. gene, into the genome of a target cell, i.e. gene therapy applications. The subject vectors may be used to deliver a wide variety of therapeutic nucleic acids. Therapeutic nucleic acids of interest include genes that replace defective genes in the target host cell, such as those responsible for genetic defect based diseased conditions; genes which have therapeutic utility in the treatment of cancer; and the like. Specific therapeutic genes for use in the treatment of genetic defect based disease conditions include genes encoding the following products: factor VIII, factor IX, β-globin, low-density protein receptor, adenosine deaminase, purine nucleoside phosphorylase, sphingomyelinase, glucocerebrosidase, cystic fibrosis transmembrane regulator, α-antitrypsin, CD-18, omithine transcarbamylase, arginosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, and the like. Cancer therapeutic genes that may be delivered via the subject vectors include: genes that enhance the antitumor activity of lymphocytes, genes whose expression product enhances the immunogenicity of tumor cells, tumor suppressor genes, toxin genes, suicide genes, multiple-drug resistance genes, antisense sequences, and the like.

Uses of adenoviral vectors are further described in U.S. Pat. Nos. 5,962,313; 5,962,311; 5,952,221; 5,932,210; 5,928,944; 5,922,576; 5,919,676; 5,891,690; 5,885,808; 5,880,102; 5,877,011; 5,871,982; 5,869,037; 5,858,351; 5,851,806; 5,843,742; 5,837,484; 5,820,868; 5,789,390; 5,756,283; 5,747,072; 5,731,172; 5,700,470; 5,670,488; 5,616,326; 5,589,377; 5,585,362; 5,354,678; the disclosures of which are herein incorporated by reference.

TRANSGENIC CELLS AND NON-HUMAN TRANSGENIC ANIMALS

Also provided by the subject invention are transgenic cells and non-human transgenic animals. A critical feature of the subject cells is the presence of the subject recombinant adenovirus in the cell, e.g. either on a vector in the cell or stably integrated the cell's genome. Similarly, the transgenic animals of the subject invention are characterized by include at least one transgenic cell, as described supra.

KITS

Also provided by the subject invention are kits for preparing the subject recombinant adneoviral genome and adenoviral vectors, as described above. The subject kits at least include a first vector and corresponding first, second and third restriction endonucleases, as described above. In addition, the subject kits may also include a shuttle vector, where the shuttle vector is characterized by including a region having the first and third restriction endonuclease sites flanking a multiple cloning site. In addition, the kit may also include a packaging cell line, e.g. an E gene transcomplementing cell line. Other optional components of the kit include: restriction enzymes, control plasmids (e.g. pAdHM10-LacZ, pAdHM4-LacZ) etc. The various components ofthe kit may be present in separate containers or certain compatible components may be precombined into a single container, as desired. In addition, the kits will generally include instructions for practicing the subject methods, where the instructions may be present on one or more of: containers present in the kit, a package insert and the packaging of the kit.

The following examples are offered by way of illustration and not by way of limitation.

EXPERIMENTAL

I. PREPARATION OF AN E1 DELETED RECOMBINANT ADENOVIRAL VECTOR

A. MATERIALS AND METHODS

1. Plasmid

Vector plasmid, pAdHM1, 2, 3 and 4, were constructed as described below. pHVAd2 (provided from HepaVec, Inc., Berlin, Germany), which has the left end (bp 1 to 341, bp 3524 to 5790) of Ad type 5 genome with E1 deletion, was cut by ClaI and EcoRI, and ligated with oligonucleotide 1 (5'-CG<u>TAACTATAACGGTCCTAAGGTAGCGAG</u>-3')

Figure 1A:
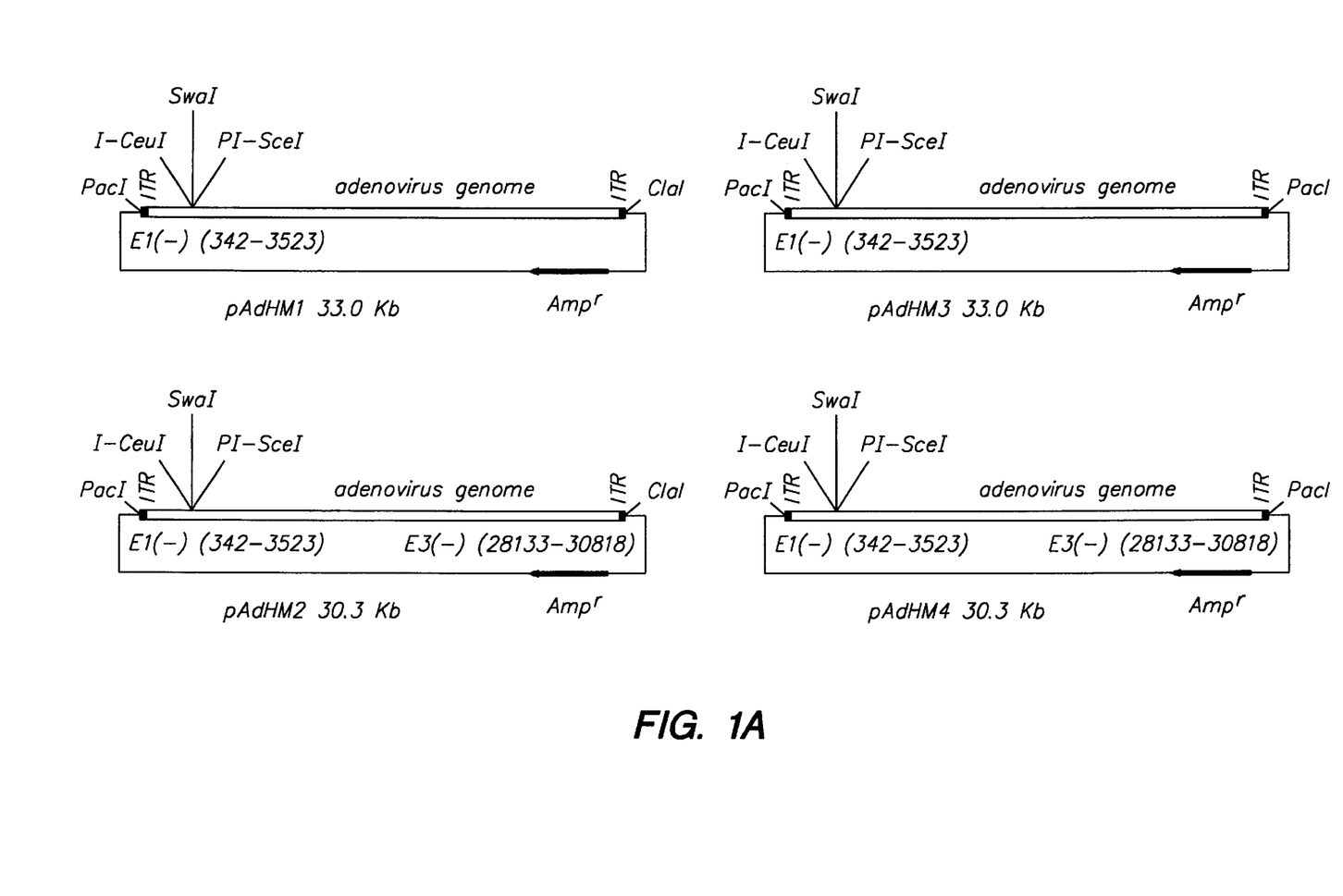
FIG. 1A provides a represenation of vector plasmids, pAdHM1, 2, 3 and4.

(SEQ ID NO:01) and 2 (5'-AATTC TCGCTACCTTAGGACCGTTATAGTTA-3'; I-CeuI recognition sequences are underlined) (SEQ ID NO:02);, resulting in pAd4. Then, pAd4 was cut with EcoRI and SalI, and then ligated with oligonucleotide 3 (5'-AATTATTTAAAT ATCTATGTCGGGTGCGGAGAAAGAGGTAATGAAAT GGCA-3') (SEQ ID NO:03) and 4 (5'-TCGA TGCCATTTCATTACCTCTTTCTCCGCACCCGACATA GATATTTAAAT-3'; PI-SceI or SwaI recognition sequences are underlined or italicized, respectively) (SEQ ID NO:04), resulting in pAd18, which contains I-CeuI, SwaI, and PI-SceI site. pAd19, which contains the Ad type 5 genome (bp 1 to 21562), was prepared by the insertion of PacI and BamHI fragment of pTG3602 (Chartier, et al.,1996, supra), which has a full length Ad type 5 genome flanked with a PacI site, in the plasmid derived from pGEM7Zf(−) (Promega Corp., Madison, USA). PacI and XcaI fragments of pAd18 and pAd19 were then ligated, resulting in pAd16. BamHI and PacI fragment (bp 21562 to right end of the genome) of pTG3602 or pHVad1 (provided from HepaVec, Inc., Berlin, Germany), which has Ad type 5 genome with a deletion in the E3 region (28133–30818), was introduced into ClaI and BamHI site of pGEM7Zf(−), after the PacI site of pTG3602 or pHVad1 was changed into ClaI site by using ClaI linker (New England Biolabs, Inc., MA, USA), resulting in pAd1 or pAd2, respectively. Then, the fragment of pAd16 digested with PacI and BamHI was cloned into NsiI and BamHI site of pAd1 or 2 after NsiI site was changed into PacI site by using PacI linker (New England Biolabs, Inc.). The resulting plasmids were named pAdHM1 or pAdHM2, respectively. The ClaI site of pAdHM1 or pAdHM2 was changed into PacI site by using oligonucleotide 5 (5'-CGTTAATTAA-3') (SEQ ID NO:05) and 6 (5'-CGTTAATTAA-3'; PacI recognition sequences are underlined) (SEQ ID NO:06), resulting in pAdHM3 or pAdHM4, respectively. pAdHM1, 2, 3 and 4 have I-CeuI, SwaI, and PI-SceI site in the E1 deletion region. pAdHM1 and 3 have the Ad genome with a deletion in the E1 region (ΔE1; bp 342 to 3523), while pAdHM2 and 4 have Ad genome with a deletion in the E1 and E3 region (ΔE1; bp 342 to 3523, ΔE3; bp 28133 to 30818). pAdHM1 and pAdHM2 have a PacI site at the left end of Ad genome and a ClaI site at the right end of the genome. pAdHM3 and pAdHM4 have PacI sites at both ends of the Ad genome (FIG. 1. A).

Figure 1B:
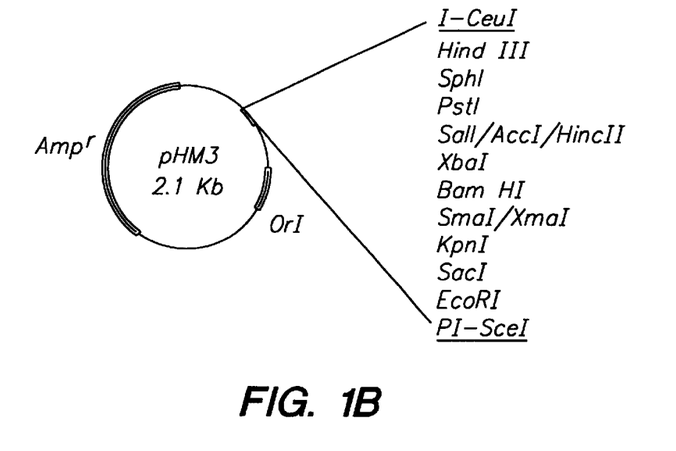
FIG. 1B provides a representation of shuttle plasmid, pHM3

Shuttle plasmid, pHM3, was constructed as described below. pUC18 was cut by AatII and HindIII, and ligated with oligonucleotide 7 (5'-TAACTATAACGGTCCTAAGGTAGCGAA-3') (SEQ ID NO:07) and 8 (5'-AGCTT TCGCTACCTTAGGACCGTTATAGTTAACGT-3'; I-CeuI recognition sequences are underlined)(SEQ ID NO:08), resulting in pHM1. pHM1 was cut with EcoRI and PvuII, and then ligated with oligonucleotide 9 (5'-AATTC TGGCAAACAGCTATTATGGGTATTATGGGT-3') (SEQ ID NO:09) and 10 (5'-ACCCATAATACCCATAATAGCTGTTTGCCAG-3'; PI-PspI recognition sequences are underlined) (SEQ ID NO:10), resulting in pHM2. This plasmid has another introncoded enzyme, PI-PspI, recognition site. Then, PI-PspI fragment of pHM2 was ligated with oligonucleotide 11 (5'-ATCTATGTCGGGTGCGGAGAAAGAGGTAATGAAAT GGCATTAT-3') (SEQ ID NO:11)and 12(5'-TGCCATTTCATTACCTCTTTCTCCGCACCCGACATA GATAAA-3'; PI-SceI recognition sequences are underlined) (SEQ ID NO:12). The resulting plasmid was named pHM3 (FIG. 1. B). pHM3 contains the pUC18-derived multi-cloning site between I-CeuI and PI-SceI site. All mutations were sequenced by Sequenase Version 2.0 DNA Sequencing Kit (New England Nuclear, Boston, MASS, USA).

Figure 1C:
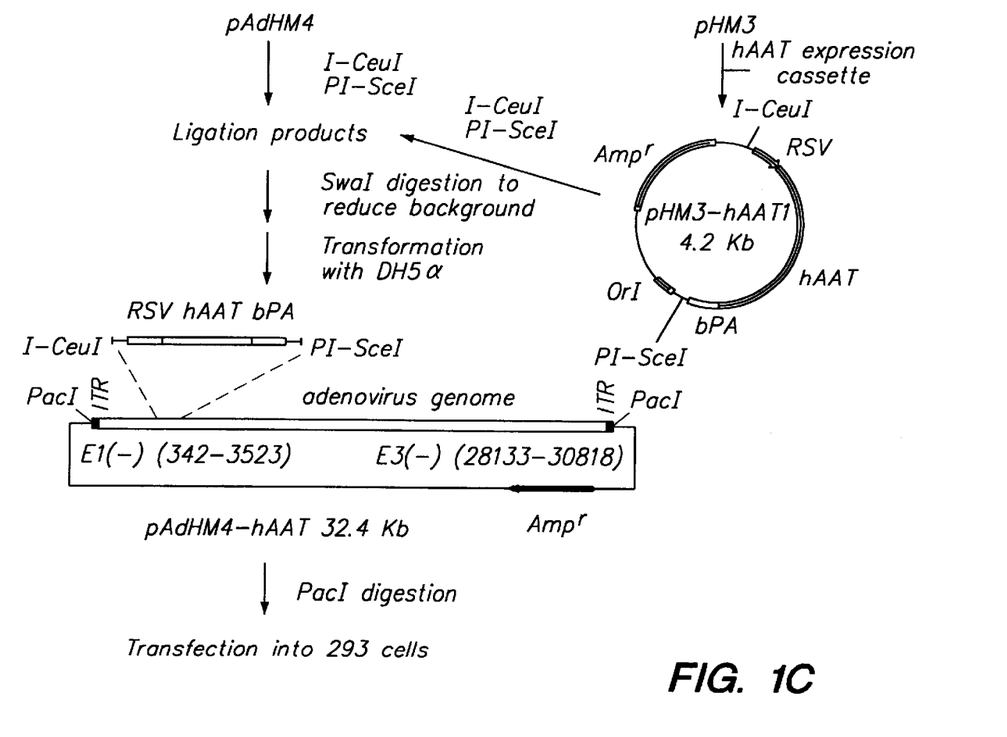
FIG. 1C provides a sheme for the construction strategy of E1 and E3 deleted adenovirus vector. The expression cassette of interest (RSVhAATbPA) was inserted into the SalI site of the multi-cloning site of pHM3, and the resulting plasmid, pHM3-hAAT1, was digested with I-CeuI and PI-SceI. The fragment containing the hAAT expression cassette was ligated with pAdHM4 digested with I-CeuI and PI-SceI. Transformation into DH5α was performed after the ligation samples were digested with SwaI to reduce the colony formation containing parental vector plasmid (pAdHM4).

2. Construction of Recombinant Ad Vector DNA Containing hAAT Expression Cassette The XhoI fragment of pBSRSVhAAT (Kay, et al., Human Gene Therapy (1992)3:641–647), containing the Rous sarcoma virus long terminal repeat (RSV-LTR) promoter, human α1-antitrypsin (hAAT) cDNA, and bovine growth hormone polyadenylation signal, was cloned into the SalI site of pHM3. Depending on the orientation of the HAAT expression cassette, the resulting plasmids were named pHM3-hAAT1 and pHM3-hAAT2 (FIG. 1C).

To construct the plasmid for a recombinant Ad vector expressing hAAT, pHM3-hAAT1 was digested with I-CeuI and PI-SceI, and the fragment containing hAAT expression cassette was isolated by the gel extraction after the agarose gel-electrophoresis. pAdHM4 was also digested with I-CeuI and PI-SceI, but the digested DNA was purified by phenol/chloroform extraction and ethanol precipitation. Then, 0.1 μg of the digested-pAdHM4 was ligated to the pHM3 fragment containing HAAT expression cassette at 16° C. for more than 2 h. To reduce the background with the parental plasmid, pAdHM4, the ligation products were treated at 65° C. for 20 min to inactivate T4 DNA ligase, and then digested with SwaI. SwaI cuts the parental plasmid (pAdHM4), but not the recombinant plasmid. Finally, the DNAs were transformed with electrocompetent DH5α (chemical competent DH5α can be also used), and the individual clones were screened by restriction analysis (FIG. 1C). Large scale preparation of plasmid, pAdHM4-hAAT, was performed by using Qiagen Plasmid Maxi Kit (Qiagen, Inc., CA, USA). No rearrangement of the plasmid during amplification was observed.

3. Generation of Adenovirus Vector pAdHM4-hAAT was linearized by the digestion with PacI and purified by phenol/chloroform extraction and ethanol precipitation. The DNA was transfected into sub-confluent-293 cells plated in 60 mm dish with SuperFect (Qiagen, Inc.) according to the manufacture's instruction. The cells were cultured with Dulbecco's modified Eagle's medium (DMEM) (Gibco, Inc.) containing 10% fetal calf serum (FCS) or with 0.5% overlayed agarose-DMEM containing 10% FCS. Ten days later, the cells were harvested and five independent plaques were isolated. The virus was released by four cycles of freezing and thawing, and amplified in 293 cells. Recombinant virus expressing hAAT was referred to as AdhAAT. Titer of the virus was measured by standard plaque assay in 293 cells (Kay, et al.,Hepatology (1995) 21: 815–819).

To analyze the viral DNA, Ad DNA was isolated from the cells with full cytopathic effect (CPE) as described previously (Lieber, et al., J. Virol. (1996) 70:8944–8960). Briefly, 293 cells with full CPE were digested with 0.1% pronase in 10 mM Tris-HCl (pH 7.5)-1% sodium dodecyl sulfate-10 mM EDTA for over night at 37° C. After phenol/chloroform extraction, DNA was ethanol precipitated, dissolved in TE (10 mM Tris (pH 7.5), 1 mM EDTA) and digested with HindIII or I-CeuI/PI-SceI, and analyzed by a 0.8% agarose gel stained with ethidium bromide.

4. hAAT Expression in HeLa Cells Infected with AdhAAT

HeLa cells (8×10$^5$ cells) were seeded into 60-mm dish, and the next day they were treated with AdhAAT (MOI=20 or 100). The cells were cultured with DMEM containing 10% FCS and 2 days later hAAT concentrations in the medium were determined by enzyme-linked immunosorbent assay as previously described (Kay, et al.,1995, supra).

B. RESULTS

1. Construction and Characterization of E1 Deleted Adenovirus Vector DNA

To construct the plasmid with a recombinant Ad vector DNA containing a foreign gene at the E1 deletion site by a single in vitro ligation, three unique restriction sites, I-CeuI, SwaI and PI-SceI, were introduced into the E1 deletion site of the vector plasmid containing a complete vector genome.

I-CeuI (Marshall, et al., Gene (1991) 104:241–25 245), PI-SceI (Gimble, et al., Nature (1992) 357:301–306 are intron-coded endonucleases that recognize at least 9–10 and 11 bp, respectively. SwaI is a rare-cutting restriction enzyme with a sequence specificity of 8 bp. I-CeuI and PI-SceI sites were used for the insertion of foreign gene, while SwaI site was used to reduce the generation of parental, non-recombined, plasmid. The resulting vector plasmid, pAdHM1, 2, 3 and 4, contain the complete Ad genome minus the E1 (pAdHM1, 3) or E1/E3 region (pAdHM2, 4), which have PacI (pAdHM3, 4) or PacI/ClaI (pAdHM 1, 2) at the both ends of Ad genome, and have I-CeuI, SwaI and PI-SceI site in the E1 deletion site (FIG. 1A). HindIII and PacI treatment of pAdHM4 produced the expected fragments upon separation in a 0.8% agarose gel following ethidium bromide staining.

A shuttle plasmid, pHM3, containing a pUC 18-derived multi-cloning site between the I-CeuI and PI-SceI sites was constructed (FIG. 1B) and used for cloning an expression cassette containing a human alpha 1-antitrypsin cDNA under the transcriptional control of the RSV-LTR promoter (RSVhAATbPA) the product of which was called (pHM3-hAAT1). The corresponding Ad vector DNA, pAdHM4-hAAT (FIG. 1C) was produced by in vitro ligation of I-CeuI/PI-SceI digested pAdHM4 and pHM3-hAATI (FIG. 1C). I-CeuI and PI-SceI digestion of pAdHM4-hAAT produced the expected 2.1 kb DNA fragment corresponding to an hAAT expression cassette in addition to the expected adenoviral fragments. The expected DNA fragments were also detected with either PacI or PacI/HindIII digestion. More than 90% (15 out of 16 clones) of the transformants had the correct restriction pattern.

2. Generation of Adenovirus Vector Expressing hAAT

To demonstrate that pAdHM4-hAAT was able to produce Ad vector in 293 cells, PacI-linearized pAdHM4-hAAT DNA was transfected into 293 cells and the cells were cultured for 10 days. The cell lysates were used to infect fresh 293 cells followed by routine adenovirus preparation. The correctness of the viral DNA was verified by double-digestion with I-CeuI and PI-SceI or HindIII digestion and found to have the same pattern as PacI/HindIII-digested pAdHM4-hAAT plasmid DNA. For further confirmation, 17 independent plaques were found to have identical DNA restriction patterns. Virus was not produced by the transfection of circular plasmid (pAdHM4-hAAT) into 293 cells, consistent with previous reports (Chartier, et al. ,1996, supra amd He, et al. ,1998, supra). Finally, to confirm functionality of the vector, robust hAAT expression was detected in AdhAAT infected Hela cells.

II. CONSTRUCTION OF AN E1/E4 DELETED ADENOVIRAL VECTOR

A. MATERIALS AND METHODS

1. Construction of Recombinant Plasmids

Vector plasmids pAdHM 10 and pAdHM12 were constructed as follows. EcoRI/BglII fragment of pEco-ITRO, which has the right end of Ad type 5 genome (27331-right end) with a BglII site instead of BsgI site, was ligated with EcoRI/MunI fragment of pBHG11 (Microbix, Toronto, Ontario, Canada) after EcoRI/BglII site of pEco-ITRO and EcoRI/MunI site of pBHG11 were changed into a NotI site by using a NotI linker, resulting in pEco-ΔE3,4. The PacI site in the E3 deletion region of pEco-ΔE3,4 was deleted (pEco-ΔE3,4P), and the HpaI/SrfI fragment of pEco-ΔE3,4P and pEco-ITR0 were ligated, resulting in pEco-ITR1. Then, the SrfI/ClaI fragment of pEco-ITR1 was inserted between the SrfI and ClaI site of pAdHM1 (Mizuguchi and Kay, Human Gene Tharap. (1998) 9:2577–2583), resulting in pAdHM9. pEco-ΔE3,4P was also cut with SrfI and ClaI, and ligated with SrfI/ClaI-digested pAdHM1, resulting in pAdHM11. The ClaI site of pAdHM9 and pAdHM11 was changed into a PacI site by using oligonucleotides 5 (5' CG TTAATTAA 3')(SEQ ID NO:13) (PacI recognition sequences are underlined). Resulting plasmids were named pAdHM10 and pAdHM12, respectively.

Shuttle plasmid pHM5 was constructed by the ligation of DraI/SspI fragment of pHM3 (Mizuguchi and Kay, 1998, supra) with NheI/BamHI fragment of pACYC177 (Nippon Gene, Toyama, Japan) after the NheI/BamHI sites were filled with Klenow fragment of DNA polymerase. pHMCMV5, -6 and pHMRSV5, -6 were constructed by using the pHM5 and the cytomegalovirus (CMV) promoter and bovine growth hormone (BGH) polyadenylation signal from pcDNA3.1/Zeo (Invitrogen. Carsbad, Calif.) or the Rous Sarcoma Virus long terminal repeat (RSV-LTR) enhancer/promoter from pREP 10 (Invitrogen), respectively. Detailed information about the constructions is available from the authors upon request.

2. Construction of E1/E3 or E1/E3/E4 Deleted Recombinant Ad Vector DNA Expressing β-galactosidase

*Escherichia coli* β-galactosidase (LacZ) gene derived from pCMVβ(Clontech, Palo Alto, Calif.) was sub-cloned into the XhoI/NotI site of pcDNA3.1/Zeo, after the SmaI site of pCMVβ was changed into a XhoI site by using a XhoI linker. Then, the LacZ gene was cloned by digestion with NotI and XbaI and inserted into the NotI/Xbal site of pHMCMV5, resulting in pHMCMVLacZ-1. pHMCMVLacZ-1, pAdHM10and pAdHM12 were digested with I-CeuI and PI-SceI, and purified by phenol-chloroform extraction and ethanol precipitation. Digested pAdHM 10 or pAdHM 12 (0.1 μg) were ligated with digested pHMCMVLacZ-1 at 16° C. for more than 2 hr. No agarose gel electrophoresis and fragment extraction were needed for both the vector and shuttle plasmid. To prevent the production of a plasmid containing a parental Ad genome, the ligation products were digested with SwaI, transformed with chemical-competent DH5α(electro-competent DH5αcan be also used) and grown in ampicillin, resulting in pAdHM10-LacZ and pAdHM12-LacZ.

3. Generation of Recombinant Virus pAdHM10-LacZ and pAdHM12-LacZ DNAs were digested with PacI, purified by phenol-chloroform extraction, and ethanol precipitation. To make an E1/E3 or E1/E3/E4 deleted Ad vector, linearized pAdHM10-LacZ or pAdHM12-LacZ were transfected into 293 cells or VK10-9 cells, which are 293 cells transformed with constructs containing the E4 transcription unit and pIX coding sequences under the control of inducible metallothionein promoter (Krougliak and Graham, 1995) (kindly provided by Dr. Valeri Krougliak, Mouni Sinai Medical Center. NY), respectively. E1/E3 deleted virus was prepared as described previously (Mizuguchi and Kay, 1998, supra). In case of E1/E3/E4 deleted Ad vector, the cells were cultured with Dulbecco's modified Eagle's medium (GIBCO, Grand Island, N.Y.) containing 10% fetal calf serum and $10^{-6}$ M (final concentration) of dexamethazone for 14 days. At this point, no cytopathic effect (CPE) was observed. The cell lysate prepared from the cells transfected by pAdHM12-LacZ was added to fresh VK10-9 cells. CPE was observed in about 7 days. Ad DNA was isolated from the cells with full cytopathic effect as described previously (Lieber, et al. ,1996, supra).

B. RESULTS AND DISCUSSION

The ampicillin resistance gene of the shuttle plasmid pHM3 (Mizuguchi and Kay, 1998, supra) was exchanged with a kanamycin resistance gene, resulting in pHM5. This plasmid was used to derive shuttle plasmids that already have the CMV or RSV promoter and BGH poly adenylation signal in both orientations. pAdHM10 and pAdHM12 were prepared for the construction of E1/E3 and E1/E3/E4 deleted vectors, respectively. pAdHM10 has larger E3 deletion than pAdHM4 (pAdHM 10, 3.1 kb; pAdHM4, 2.6 kb). Up to 4.9 kb, 7.6 kb, 8.1 kb, and 10.9 kb of exogenous DNA can be introduced into pAdHM3, –4, –10, –12, respectively.

The CMV promoter-driven LacZ expressing E1/E3 and E1/E3/E4 deleted Ad vectors was constructed as a representative example. First, the LacZ gene was inserted into the multicloning site of pHMCMV5, resulting in pHMCMVLacZ-1. Second, pHMCMVLacZ-1 and vector plasmids (pAdHM10 and pAdHM12) were digested with I-CeuI and PI-SceI, and directly ligated without gel purification of either the LacZ expression cassette sequence and vector viral sequence. Third, the ligation products were digested with SwaI, transformed with DH5α, and selected with ampicillin. SwaI digestion cut parental vector plasmid, but not the expected recombinant plasmid. Only the ligated Ad plasmid DNAs with the LacZ expression cassette were selected for. More than 75% of the transformants (7 of 9 clones) had the correct insert as determined by restriction digestion. Fourth, recombinant plasmid, pAdHM10-LacZ or pAdHM12-LacZ was cleaved with PacI, and directly transfected into 293 cells or 293 cells expressing E4 gene product (VK10-9) (Krougliak and Graham, Human Gene Therap. (1995) 6:1575–1586), resulting in a homogeneous population of recombinant E1/E3 or E1/E3/E4 deleted vector expressing LacZ (AdHM10-LacZ or AdHM12-LacZ), respectively. DNA restriction analysis showed that vector plasmid with or without the LacZ expression cassette and viral DNA (AdHM 10-LacZ or AdHM12-LacZ) contained the expected fragments.

Finally, to confirm the functionality of the vector, HeLa cells were found to be equally transducible with either the AdHM 10-LacZ and AdHM12-LacZ vector as determined by X-gal staining.

It is evident from the above results and discussion that a simple and efficient method for constructing recombinant E gene deleted adenoviral vectors by in vitro ligation is provided by the subject invention. The present invention does not suffer from manipuation difficulties experienced in prior art in vitro methods, such as low efficiency, etc. The present methods also escape the inefficiencies of homologous recombination based methods. The major advantages of the present invention include the simplicity of requiring only a routine 2 step transformation protocol that is familiar to any molecular biologist. Furthermore, because of the paucity of generation of wildtype or null vectors, the time-consuming plaque purification procedure is not absolutely required to produce virus. In addition, the subject methods allow for the easy modification of vector DNA backbone or addition of various expression cassettes by routine cloning for construction because of the many unique restriction sites in pAdHM1 or pAdHM2. In addition, the subject methods allow for the production of vectors which have proven difficult to make if they produce a protein that interferes with DNA recombination, or cell viability with prolonged expression in mammalian cells. In general, the use of the subject methods facilitates the construction of additional Ad vectors for the gene transfer in basic research as well as gene therapy. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of preparing a recombinant adenoviral genome having an insertion nucleic acid located in an E gene region of said genome, said method comprising:
   (a) providing a first vector comprising an adenoviral genome having an E gene region with a deletion of 1.0 to 12.0 kb, where said first vector is further characterized by having first, second and third restriction endonuclease sites, wherein said second restriction endonuclease site is flanked by said first and third restriction endonuclease sites, wherein each of said first, second and third restriction endoncuclease sites are: (i) different, (ii) do not occur in the corresponding wild type adenoviral genome and (iii) are located in said E gene region;
   (b) providing a second vector comprising an insertion nucleic acid flanked by said first and third restriction endonuclease sites;
   (c) contacting each of said first and second vectors with said first and third restriction endonucleases to produce first and second restriction endonuclease cleavage products, wherein said first cleavage product comprises said adenoviral genome and said second cleavage product comprises said insertion nucleic acid;
   (d) combining said first and second cleavage products under ligation conditions sufficient to produce a ligation product composition comprising a ligation product that includes said recombinant adenoviral genome having an insertion nucleic acid located in an E gene region of said genome;
   whereby said recombinant adenoviral genome having an insertion nucleic acid located in an E gene region of said genome is produced.

2. The method according to claim 1, wherein said method further comprises contacting said ligation product composition with said second restriction endonuclease.

3. The method according to claim 1, wherein said first and second vectors are plasmids.

4. The method according to claim 1, wherein said ligation product is a plasmid.

5. The method according to claim 1, wherein said E gene region is characterized by having a deletion of at least one of an E1, E3 and E4 region.

6. The method according to claim 1, wherein said first, second and third restriction endonucleases are selected from the group consisting of I-CeuI, PI-SceI and SwaI.

7. The method according to claim 1, wherein said second vector is subjected to a purification step prior to said combining step.

8. The method according to claim 1, wherein said second vector is not subjected to a purification step prior to said combining step.

9. A method of preparing a recombinant adenoviral genome having an insertion nucleic acid located in an E gene region of said genome, said method comprising:
(a) providing a first plasmid comprising an adenoviral genome having an E gene region characterized by a deletion of at least one of an E1, E3 and E4 gene, where said first plasmid is further characterized by having first, second and third restriction endonuclease sites wherein said second restriction endonuclease site is flanked by said first and third restriction endonuclease sites, wherein each of said first, second and third restriction endoncuclease sites are: (i) different, (ii) are selected from the group consisting of I-CeuI, PI-SceI and SwaI and (iii) are located in said E gene region;
(b) providing a second plasmid comprising an insertion nucleic acid flanked by said first and third restriction endonuclease sites;
(c) contacting each of said first and second vectors with said first and third restriction endonucleases to produce first and second cleavage products, wherein said first cleavage product that includes said adenoviral genome and said second cleavage product comprises said insertion nucleic acid;
(d) combining said first and second cleavage products under ligation conditions sufficient to produce a ligation product composition comprising plasmid comprising said recombinant adenoviral genome having an insertion nucleic acid located in an E gene region of said genome; and
(e) contacting said ligation product composition with said second restriction endonuclease;
whereby said recombinant adenoviral genome having an insertion nucleic acid located in an E gene region of said genome is produced.

10. The method according to claim 9, wherein said insertion nucleic acid encodes a product.

11. The method according to claim 9, wherein said method further comprises isolating said second cleavage product prior to said combining step.

12. The method according to claim 9, wherein said adenoviral genome is an AD type 5 genome.

13. A method of preparing a recombinant adenoviral genome having an insertion nucleic acid located in an E gene region of said genome, said method comprising:
(a) providing a first plasmid comprising an adenoviral genome having an E gene region characterized by a deletion of at least one of an E1, E3 and E4 gene, where said first plasmid is further characterized by having first, second and third restriction endonuclease sites wherein said second restriction endonuclease site is flanked by said first and third restriction endonuclease sites, wherein each of said first, second and third restriction endoncuclease sites are: (i) different, (ii) are selected from the group consisting of I-CeuI, PI-SceI and SwaI and (iii) are located in said E gene region;
(b) providing a second plasmid comprising an insertion nucleic acid flanked by said first and third restriction endonuclease sites;
(c) contacting each of said first and second vectors with said first and third restriction endonucleases to produce first and second cleavage products, wherein said first cleavage product that includes said adenoviral genome and said second cleavage product comprises said insertion nucleic acid;
(d) isolating said second cleavage product;
(e) combining said first and second cleavage products under ligation conditions sufficient to produce a ligation product composition comprising plasmid comprising said recombinant adenoviral genome having an insertion nucleic acid located in an E gene region of said genome; and
(f) contacting said ligation product composition with said second restriction endonuclease;
whereby said recombinant adenoviral genome having an insertion nucleic acid located in an E gene region of said genome is produced.

14. The method according to claim 13, wherein said adenoviral genome is an AD type 5 genome.

15. A method of preparing a recombinant adenoviral genome having an insertion nucleic acid located in an E gene region of said genome, said method comprising:
(a) providing a first plasmid comprising an AD type 5 genome having an E gene region characterized by a deletion of at least one of an E1, E3 and E4 gene, where said first plasmid is further characterized by having first, second and third restriction endonuclease sites wherein said second restriction endonuclease site is flanked by said first and third restriction endonuclease sites, wherein each of said first, second and third restriction endoncuclease sites are: (i) different, (ii) are selected from the group consisting of I-CeuI, PI-SceI and SwaI and (iii) are located in said E gene region;
(b) providing a second plasmid comprising an insertion nucleic acid flanked by said first and third restriction endonuclease sites;
(c) contacting each of said first and second vectors with said first and third restriction endonucleases to produce first and second cleavage products, wherein said first cleavage product that includes said adenoviral genome and said second cleavage product comprises said insertion nucleic acid;
(d) isolating said second cleavage product;
(e) combining said first and second cleavage products under ligation conditions sufficient to produce a ligation product composition comprising plasmid comprising said recombinant adenoviral genome having an insertion nucleic acid located in an E gene region of said genome; and
(f) contacting said ligation product composition with said second restriction endonuclease;
whereby said recombinant adenoviral genome having an insertion nucleic acid located in an E gene region of said genome is produced.

* * * * *

SEQUENCE LISTING

<160> NUMBER OF SEQ ID NOS: 13

<210> SEQ ID NO 1
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 1
cgtaactata acggtcctaa ggtagcgag                                      29

<210> SEQ ID NO 2
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 2
aattctcgct accttaggac cgttatagtt a                                   31

<210> SEQ ID NO 3
<211> LENGTH: 51
<212> TYPE: DNA

-continued

<213> ORGANISM: Artificial Sequence
<220> FEATURE:
<223> OTHER INFORMATION: synthetic oligonucleotide

<400> SEQUENCE: 3
aattatttaa atatctatgt cgggtgcgga gaaagaggta atgaaatggc a        51

<210> SEQ ID NO 4
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 4
tcgatgccat ttcattacct ctttctccgc acccgacata gatatttaaa t        51

<210> SEQ ID NO 5
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 5
cgttaattaa                                                       10

<210> SEQ ID NO 6
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 6
cgttaattaa                                                       10

<210> SEQ ID NO 7
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 7
taactataac ggtcctaagg tagcgaa                                    27

<210> SEQ ID NO 8
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 8
agctttcgct accttaggac cgttatagtt aacgt                           35

<210> SEQ ID NO 9
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 9
aattctggca aacagctatt atgggtatta tgggt                           35

```
<210> SEQ ID NO 10
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 10
acccataata cccataatag ctgtttgcca g                              31

<210> SEQ ID NO 11
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 11
atctatgtcg ggtgcggaga aagaggtaat gaaatggcat tat                 43

<210> SEQ ID NO 12
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 12
tgccatttca ttacctcttt ctccgcaccc gacatagata taa                 43

<210> SEQ ID NO 13
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 13
cgttaattaa                                                      10
```